(12) United States Patent
Kingsman et al.

(10) Patent No.: US 6,924,123 B2
(45) Date of Patent: *Aug. 2, 2005

(54) LENTIVIRAL LTR-DELETED VECTOR

(75) Inventors: Alan John Kingsman, Appleton (GB); Susan Mary Kingsman, Appleton (GB)

(73) Assignee: Oxford BioMedica (UK) Limited, Oxford (GB)

(*) Notice: Subject to any disclaimer, the term of this patent is extended or adjusted under 35 U.S.C. 154(b) by 186 days.

This patent is subject to a terminal disclaimer.

(21) Appl. No.: 10/324,616

(22) Filed: Dec. 20, 2002

(65) Prior Publication Data

US 2003/0113920 A1 Jun. 19, 2003

Related U.S. Application Data

(63) Continuation-in-part of application No. 09/254,832, filed as application No. PCT/GB97/02969 on Oct. 28, 1997, now Pat. No. 6,541,219.

(30) Foreign Application Priority Data

Oct. 29, 1996 (GB) .............................................. 9622500

(51) Int. Cl.$^7$ ....................... C12P 21/00; C12N 15/867; C12N 5/10; A61K 48/00

(52) U.S. Cl. ................ 435/69.1; 435/320.1; 435/235.1; 435/325; 435/366; 424/93.1; 424/93.2; 424/93.6

(58) Field of Search ............................... 424/93.1, 93.2, 424/93.6; 435/235.1, 320.1, 69.1, 325, 366

(56) References Cited

U.S. PATENT DOCUMENTS

| | | | |
|---|---|---|---|
| 5,344,923 A | 9/1994 | Verma et al. | |
| 5,359,035 A | 10/1994 | Habermann | |
| 5,604,114 A | 2/1997 | Haseltine et al. | |
| 6,235,522 B1 * | 5/2001 | Kingsman et al. | ........ 435/320.1 |
| 6,541,219 B1 * | 4/2003 | Kingsman et al. | .......... 435/69.1 |

FOREIGN PATENT DOCUMENTS

| | | |
|---|---|---|
| WO | WO 89/12109 | 12/1989 |
| WO | WO 92/07945 | 5/1992 |
| WO | WO 92/21750 | 12/1992 |
| WO | WO 94/12520 | 6/1994 |
| WO | WO 95/28493 | 10/1995 |
| WO | WO 95/30755 | 11/1995 |
| WO | WO 95/32300 | 11/1995 |
| WO | WO 95/34670 | 12/1995 |
| WO | WO 96/05319 | 2/1996 |
| WO | WO 96/14332 | 5/1996 |
| WO | WO 96/28563 | 9/1996 |
| WO | WO 96/37621 | 11/1996 |
| WO | WO 96/37623 | 11/1996 |
| WO | WO 97/18319 | 5/1997 |
| WO | WO 97/48277 | 12/1997 |

OTHER PUBLICATIONS

Brenner et al., Biochimica et Biophysica Acta, 2003, vol. 1640, pp. 1–24.*
Marshall, Science, 2003, vol. 299, p. 320.*
Kmeic, American Scientist, 1999, vol. 87, pp. 240–247.*
Fox, Nature Biotechnology, 2000, vol. 18, pp. 143–144.*
Anderson, Nature, 1998, vol. 392, pp. 25–30.*
Quinonez et al., DNA and Cell Biology, 2002, vol. 21, No. 12, pp. 937–951.*
Chang et al. (1993) Human Immunodeficiency Viruses Containing Heterologous Enhancer/Promoter are Replication Competent and Exhibit Different Lymphocyte Tropisms. Journal of Virology, vol. 67, pp. 743–752.
Verma et al. (1997) Gene Therapy–Promises, Problems, and Prospects. Nature, vol. 39, pp. 239–242.
Eck et al. (1996) "Gene–Based Therapy. Goodman & Gilman's The Pharmacological Basis of Therapeutics, 9$^{th}$ Ed., Chapter 5".
Paulus et al. "Self–contained, Tetracycline–Regulated Retroviral Vector System for Gene Delivery to Mammalian Cells," Journal of Virology, vol. 70(I), Jan. 1996, pp. 62–67.
Parolin et al. (1996) "Use of cis– and trans–Acting Viral Regulatory Sequences To Improve Expression of Human Immunodeficiency Virus Vectors In Human Lymphocytes," Virology, vol. 222, pp. 415–522.
Marasco et al., "Design, intracellular expression, and activity of a human anti–human immunodeficiency virus type 1 gp120 single–chain antibody", Proc. Natl. Acad. Sci, vol. 90, 1993, Natl. Acad. Sci., Washington, D.C.
Nature–Genetics, vol. 8, Oct. 1994, pp. 148–154, Kaplitt et al., "Long–term gene expression and phenotypic correction using adeno–associated virus vectors in the mammalian brain".
Science, vol. 266, Nov. 25, 1994, pp. 1399–1403, During et al., "Long–Term Behavioral Recovery in Parkinsonian Rats by an HSV Vector Expressing Tyrosine Hydroxylase".
Neuroreport, vol. 6, No. 1, Dec. 30, 1994, Horellou et al., "Direct intracerebral gene transfer of an adenoviral vector expressing tyrosine hydroxylase in a rat model of Parkinson's disease".
Journal of Neurochemistry, vol. 56, No. 3, 1991, pp. 1030–1036, Owens et al., "L–3, 4–Dihydroxyphenylaianine Synthesis by Geneticall Modified Schwann Cells".

(Continued)

Primary Examiner—David Guzo
(74) Attorney, Agent, or Firm—Frommer Lawrence & Haug; Thomas J. Kowalski

(57) ABSTRACT

A vector capable of transducing non-dividing and/or slowly dividing cells is provided, wherein the vector is a lentiviral LTR-deleted vector. Also provided is a method for producing a protein of interest in a non-dividing or slowly dividing cell by transducing the cell with a lentiviral LTR-deleted vector and expressing the protein of interest in the cell. In addition, target cells containing the lentiviral LTR-deleted vector are provided.

6 Claims, 6 Drawing Sheets

OTHER PUBLICATIONS

Science, vol. 272, Apr. 12, 1996, pp. 263–267, Naldini et al., "In Vivo Gene Delivery and Stable Transduction of Nondividing Cells by a Lentiviral Vector".

Journal of Virology, Jul. 1988, pp. 2464–2473, Bowtell et al., "Comparison of Expression in Hemopoietic Cells by Retroviral Vectors Carrying Two Genes".

Blood, vol. 84, No. 6, Sep. 15, 1994, pp. 1812–1822, Correli et al., "Retroviral Vector Design for Long–Term Expression in Murine Hematopoietic Cells In Vivo".

Cell, vol. 39, Dec. 1984, pp. 459–467, Emermann et al., "Genes with Promoters in Retrovirus Vectors Can Be Independently Suppressed by an Epigenetic Mechanism".

Molecular and Cellular Biology, Dec. 1991, pp. 5848–5859, Ghattas et al., "The Encephalomyocarditis Virus Internal Ribosome Entry Site Allows Efficient Coexpression of Two Genes from a Recombinant Provirus in Cultered Cells and in Embryos".

Proc. Natl. Acad. Sci. USA, vol. 86, May 1989, pp. 3519–3523, Hantzopoulos et al., "Improved gene expression upon transfer of the adenosine deaminase minigene outside the transcriptional unit of retroviral vector".

The Journal of Biological Chemistry, vol. 266, No. 13, May 5, 1991, pp. 8416–8425, Hatzoglou et al., "Hormonal Control of Interacting Promoters Introduced into Cells by Retroviruses".

The Journal of Biological Chemistry, vol. 263, No. 33, Nov. 25, 1988, pp. 17798–17808, Hatzoglou et al., "Hormonal Regulation of Chimeric Genes Containing the Phosphoenolpyrusvate Carboxykinase Promoter Regulatory Region in Hepatoma Cells Infected by Murine Retroviruses".

Human Gene Therapy 3, 1992, pp. 381–390, Li et al, "Compariosn of the Expression of a Mutant Dihydrofolate Reductase under Control of Different Internal Promoters in Retroviral Vectors".

Virology 195, 1993, pp. 1–5, McLachlin et al., "Factors Affecting Retroviral Vector Function and Structural Integrity".

Molecular and Cellular Biology, Apr. 1988, pp. 1803–1808, Overell et al., "Stably Transmitted Triple—Promoter Retroviral Vectors and Their use in Transformation of Primary Mammalian Cells".

Proc. Natl. Acad. Sci. USA, vol. 88, Jun. 1991, pp. 4626–4630, Scharfmann et al., "Long–term in vivo expression of retrovirus–mediated gene transfer in mouse fibroblast implants".

Gene Therapy, 1994 1, pp. 307–316, Vile et al., "A comparison of the properties of different retroviral vectors containing the murine tyrosinase promoter to achieve transcriptionally targeted expression of the HSVtk or Il–2 genes".

Virology 171, 1989, pp. 331–341, Xu et al. "Factors Affecting Long–Term Stability of Moloney Murine Leukemia Virus–Based Vectors".

Proc. Natl. Acad. Sci. USA, vol. 84, Aug. 1987, pp. 5197–5201, Yee et al., "Gene expression from transcriptionally disabled retroviral vectors".

Journal of Virology, Sep. 1991, pp. 4985–4990, Adam et al., "Internal Initiation of Translation in Retroviral Vectors Carrying Piconavirus 5' Nontranslated Regions".

Proc. Natl. Acad. Sci. USA, Aug. 1993, vol. 90, pp. 7889–7893, Marasco et al., "Design, intracellular expression, and activity of a human anti–human immunodeficiency virus type 1 gp120, single–chain antibody".

Cell, vol. 54, Sep. 9, 1988, pp. 841–853, Wiederrecht et al., "Isolation of the Gene Encoding the *S. cerevisiae* Heat Shock Transcription Factor".

Nature, vol. 362, Apr. 29, 1993, pp. 852–855, Dekker et al., Solution structure of the POU–specific DNA–binding domain of Oct–1.

Genes & Development 1, 1988, pp. 1582–1599, Sturm et al., "The ubiquitous octamer–binding protein Oct–1 contains a POU domain with a homeo box subdomain".

FEBST Letters, vol. 262, No. 1, Mar. 1990, pp. 82–86, Aumailley et al., "Identification of the Arg–Gly–Asp sequence in laminin A chain as a latent cell–binding site being exposed in fragment P1".

Gene Tehrapy 1995, 2, pp. 750–756, Wickham et al, "Targeting of adenovirus penton base to new receptors through replacemnt of its RGD motif with other receptor–specific peptide motifs".

Proc. Natl. Acad. Sci. USA, vol. 83, May 1986, pp. 3194–3198, Yu et al., "Self–inactivating retroviral vectors designed for transfer of whole genes into mammalian cells".

Research Paper, Dec. 1995, pp. 315–324, Haas et al., "Codon usage limitation in the expression of HIV–1 envelope glycoprotein".

Letters of Nature, vol. 326, Apr. 1987, pp. 707–711, Grima et al., "A single human gene encoding multiple tyrosine hydroxylases with different predicted functional characteristics".

Biochemical and Biophysical Research Communications, vol. 146, No. 3, 1987, pp. 971–975, Kaneda et al, "Isolation of a novel cDNA clone for human tyrosine hydroxylase: Alternative RNA splicing produces four kind of mRNA from A single gene".

Proc. Natl. Acad. Sci. USA, vol. 92, Aug. 1995, pp. 7570–7574, Somia et al., "Generation of targeted retroviral vectors by using single–chain variable fragment: An approach to in vivo gene delivery".

Analytical Biochemistry 43, 1971, pp. 588–600, Waymire et al., "Assay of Tyrosine Hydroxylase by Coupled Decarboxylation of Dopa Formed from I–$^{14}$C–L–Tyrosine".

CSH Retrovirus Meeting abstract, 1996, Srinivasakumar et al., p. 318, "Requirement for Efficient Transfer of HIV–1 Vectors to target Cells using HIV–1 Based Packaging Cell".

Nature, vol. 293, Oct. 1981, p. 543–548, Shinnick et al, "Nucleotide sequence of Moloney murine leukaemia virus".

Nucleic. Acids Research, 1995, vol. 23, No. 4, Soneoka et al, "A transient three–plasmid expression system for the production of high tilter retroviral vectors".

Biotechniques 7, 1989, pp. 980–990, Miller et al., "Improved Retroviral Vectors for Gene Transfer and Expression".

Proc. Natl. Acad. Sci., USA, 1993, vol. 90, pp. 7889–7893, Marasco et al., "Design, intracellular expression, and activity of a human anti–human, immunodeficiency virus type 1 gp120 single–chain anti–body".

Analytical Biochemistry, 1984, vol. 139, pp. 73–76, Maria Anna Rosei et al., "Oxygraphic Assay of 3, 4–Dihydroxyphenylalanine Decarboxylase Activity by Coupled Reaction with Free and Immobilized Serum Amine Oxidase".

* cited by examiner

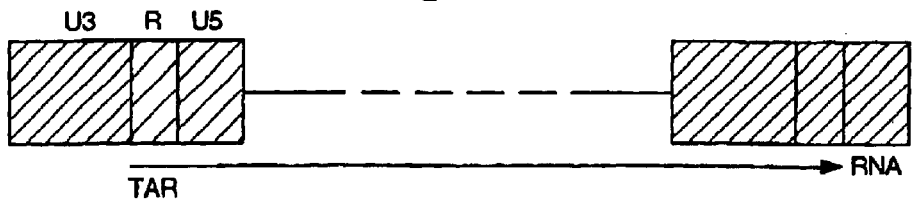
Fig. 1
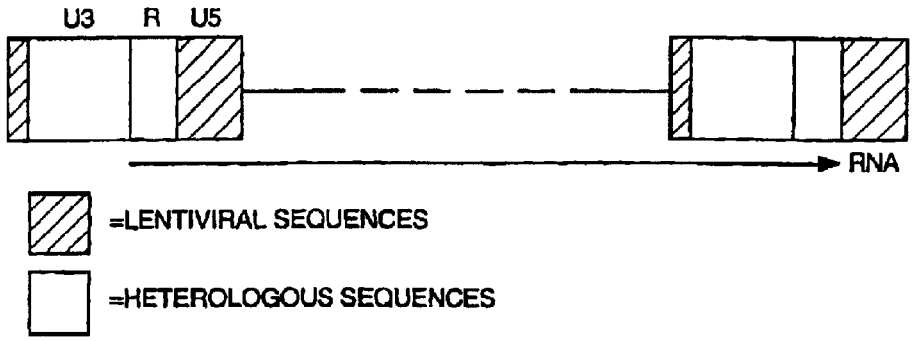
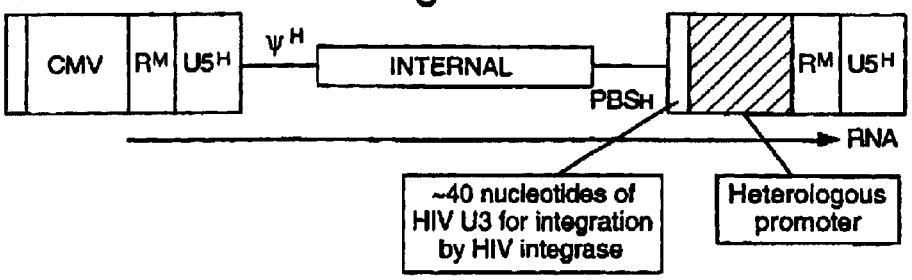
Fig. 2
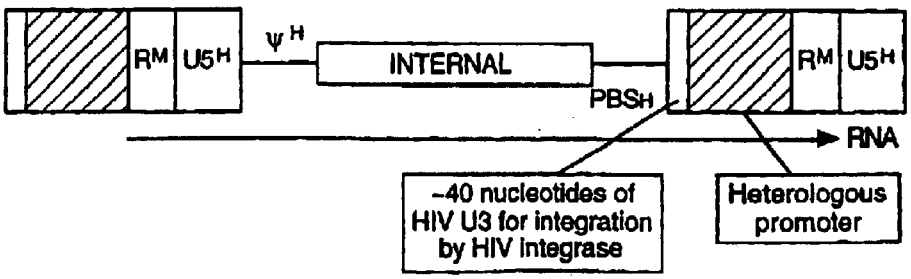

Fig. 9
PCR Primers

1) The thdd gene:

```
              HincII
TH5-1   CA CAG TCG ACC ATG CCC ACC CCC GAC GCC ACC A
                                        [SEQ ID NO:13]
              HindIII
TH3-1   CG TAC AAG CTT CGA TCC tcc acc tcc cga GCC ACC
        TCC GCC TGA ACC GCC TCC ACC GCC AAT GGC ACT CAG
        CGC ATG                         [SEQ ID NO:14]
              HindIII
DD5-1   AC GCA AAG CTT ATG AAC GCA AGT GAA TTC CGA
                                        [SEQ ID NO:15]
            SpeI
DD3-1   C TGG ACT AGT CTA CTC CCT CTC TGC TCG CAG CAC
                                        [SEQ ID NO:16]
```

2) The ddth gene:

```
              HincII
DD5-2   CA CAG TCG ACC ATG AAC GCA AGT GAA TTC CGA
                                        [SEQ ID NO:17]
              HindIII
DD3-2   CG TAC AAG CTT CGA TCC tcc acc tcc cga GCC
        ACC TCC GCC TGA ACC GCC TCC ACC CTC CCT CTC
        TGC TCG CAG CAC                 [SEQ ID NO:18]
              HindIII
TH5-2   AC GCA AAG CTT ATG CCC ACC CCC GAC GCC ACC A
                                        [SEQ ID NO:19]
            SpeI
TH3-2   C TGG ACT AGT CTA GCC AAT GGC ACT CAG CGC ATG
                                        [SEQ ID NO:20]
```

LENTIVIRAL LTR-DELETED VECTOR

RELATED APPLICATIONS

This application is a continuation-in-part of U.S. application Ser. No. 09/254,832, filed on Jun. 21, 1999 now U.S. Pat. No. 6,541,219, as the national phase application of International application Serial No. PCT/GB97/02969, filed on Oct. 28, 1997 and claiming priority to UK application Serial No. GB 9622500.8, filed on Oct. 29, 1996. This application makes reference to U.S. Pat. No. 6,235,522, filed on Apr. 5, 1999 as the national phase application of International application Serial No. PCT/GB97/02858, filed on Oct. 17, 1997 and claiming priority to UK application Serial No. GB 9621680. This application also makes reference to: U.S. Pat. No. 6,096,538, filed on Nov. 19, 1997, U.S. Pat. No. 6,132,731, filed on Oct. 8, 1997, U.S. Pat. No. 6,168,916, filed on Oct. 21, 1998, U.S. Pat. No. 6,312,682, filed on Dec. 28, 1998, U.S. Pat. No. 6,312,683, filed on Jan. 27, 1999, U.S. application Ser. No. 09/533,276, filed on Mar. 22, 2000, U.S. application Ser. No. 09/533,295, filed on Mar. 22, 2000, U.S. application Ser. No. 09/552,950, filed on Apr. 20, 2000, U.S. application Ser. No. 09/860,996, filed on May 18, 2001, U.S. application Ser. No. 09/867,947, filed on May 29, 2001, U.S. application Ser. No. 09/915,169, filed on Jul. 25, 2001, U.S. application Ser. No. 10/001,220, filed on Nov. 15, 2001, U.S. application Ser. No. 10/002,598, filed on Nov. 15, 2001, and U.S. application Ser. No. 10/008,610, filed on Nov. 8, 2001.

Each document cited or referenced in each of the foregoing applications, and any manufacturer's instructions or catalogues for any products cited or mentioned in each of the foregoing applications and in any of the cited documents, are hereby incorporated herein by reference. Furthermore, all documents cited in this text, all documents cited or referenced in documents cited in this text, and any manufacturer's instructions or catalogues for any products cited or mentioned in this text or in any document incorporated into this text, are incorporated herein by reference. Documents incorporated by reference into this text or any teachings therein can be used in the practice of this invention. Documents incorporated by reference into this text are not admitted to be prior art.

FIELD OF THE INVENTION

This invention relates to lentiviral long terminal repeat (LTR)-deleted vectors. The invention also relates to lentiviral LTR-deleted vectors carrying nucleotide sequences of interest, and to their use in transferring genetic material to non-dividing or slowly dividing cells.

BACKGROUND OF THE INVENTION

Amongst nucleic acid transfer systems, retroviral vectors hold substantial promise for gene therapy and other applications in which transfer of genetic material is desirable. These systems can transfer genes efficiently, and new vectors are emerging that are particularly useful for gene delivery to brain cells (Naldini et al., 1996 Science 272, 263).

There has been considerable interest in the development of retroviral vector systems based on lentiviruses, a small subgroup of the retroviruses. This interest arises firstly from the notion of using HIV-based vectors to target anti-HIV therapeutic genes to HIV susceptible cells and secondly from the prediction that, because lentiviruses are able to infect non-dividing cells (Lewis & Emerman 1993 J. Virol. 68, 510), vector systems based on these viruses are able to transduce non-dividing cells (e.g. Vile & Russel 1995 Brit. Med. Bull. 51, 12). Vector systems based on HIV have been produced (Buchschacher & Panganiban 1992 J. Virol. 66, 2731) and have been used to transduce CD4+ cells and non-diving cells (Naldini et al., 1996 Science 272, 263). However, in general, nucleic acid transfer efficiencies are not as high as with comparable murine retrovirus vector systems.

The HIV-based vectors produced to date result in an integrated provirus in the transduced cell that has HIV LTRs at its ends. This limits the use of these vectors as the LTRs have to be used as expression signals for any inserted gene unless an internal promoter is used. The use of internal promoters has significant disadvantages. For example, the presence of internal promoters can affect the transduction titres obtainable from a packaging cell line and the stability of the integrated vector.

Also, HIV and other lentiviral LTRs have virus-specific requirements for nucleic acid expression. For example, the HIV LTR is not active in the absence of the viral Tat protein (Cullen 1995 AIDS 9, S19). It is desirable, therefore, to modify or delete the LTRs in such a way as to change the requirements for nucleic acid expression. In particular, tissue specific gene expression signals may be required for some gene therapy applications. In addition, signals that respond to exogenous signals may be necessary. In murine retroviruses this is often achieved simply by replacing the enhancer-like elements in the U3 region of the murine lentiviral (MLV) LTR by enhancers that respond to the desired signals. This has not been feasible with viruses such as HIV because within the U3 and R regions of their LTRs are sequences, known as IST and TAR, which may inhibit gene expression and may or may not be responsive to Tat protein when heterologous, perhaps tissue specific, control sequences are inserted in the U3 region (Cullen 1995 AIDS 9, S19; Alonso et al., 1994 J. Virol. 68, 6505; Ratnasabapathy et al., 1990 4, 2061; Sengupta et al., 1990 PNAS 87, 7492; Parkin et al., 1988 EMBO. J 7, 2831). Even if the signals are responsive, it is undesirable to have to supply Tat as it further complicates the system and Tat has some properties of oncoproteins (Vogel et al., 1988 Nature 335, 606).

Parkinson's disease (PD) is a common neurodegenerative disorder that afflicts the growing population of elderly people. Patients display tremor, cogwheel rigidity and impairment of movement. It is generally thought to be an acquired rather than inherited disease in which environmental toxins, metabolic disorders, infectious agents and normal aging have all been implicated. PD is associated with the degeneration of nigrostriatal neurons which have their soma located in the substantia nigra. They send axonal projections to the basal ganglia and they use dopamine as their neurotransmitter. Some features of the disease can be controlled by the administration of L-DOPA, the metabolic precursor to dopamine, which diffuses across the blood brain barrier more effectively than dopamine itself. Unfortunately as the disease progresses the side effects of this treatment become unacceptable.

PD is an ideal candidate for gene therapy for several reasons. The clinical efficacy of systemic administration of L-DOPA suggests that restoration of neuronal circuitry is not essential for disease management. Therefore genetic manipulation of brain cells to provide local production of L-DOPA from tyrosine may be a realistic strategy for treatment. The biosynthesis of L-DOPA from tyrosine involves a single step suggesting that provision of tyrosine hydroxylase (TH) by genetic means may be sufficient and some success has been achieved using this strategy in small animals and in cell culture (Kaplitt et al., 1994 Nature Genetics 8, 148; During et al., 1994 Science 266, 1399; Horellou et al., 1994 Neuroreport 6, 49; Owens et al., 1991 J. Neurochem. 56, 1030). However, if one is to use local endogenous brain cells as L-DOPA factories for the treatment of PD in man it is likely that high levels of L-DOPA will be required to effect a treatment. These high levels must be efficiently converted to dopamine as the necessary neurotransmitter and primary therapeutic agent. It is likely therefore that it will be necessary not only to supply tyrosine hydroxylase but also DOPA decarboxylase (DD), the enzyme that converts L-DOPA to dopamine. This means that in a gene therapy strategy the genes for both of these enzymes will be required. However, it is clear from the literature that retroviral vectors achieve the highest titres and most potent gene expression properties if they are kept genetically simple (PCT/GB96/01230; Bowtell et al., 1988 J. Virol. 62, 2464; Correll et al., 1994 Blood 84, 1812; Emerman and Temin 1984 Cell 39, 459; Ghattas et al., 1991 Mol.Cell.Biol. 11, 5848; Hantzopoulos et al., 1989 PNAS 86, 3519; Hatzoglou et al., 1991 J. Biol. Chem 266, 8416; Hatzoglou et al., 1988 J. Biol. Chem 263, 17798; Li et al., 1992 Hum. Gen. Ther. 3, 381; McLachlin et al., 1993 Virol. 195, 1; Overell et al., 1988 Mol. Cell Biol. 8, 1803; Scharfman et al., 1991 PNAS 88, 4626; Vile et al., 1994 Gene Ther 1, 307; Xu et al., 1989 Virol. 171, 331; Yee et al., 1987 PNAS 84, 5197). This means only using a single transcription unit within the vector genome and orchestrating appropriate nucleic acid expression from sequences within the 5' LTR. The need to express two enzymes from a single retroviral vector would require the use of an internal ribosome entry site (IRES) to initiate translation of the second coding sequence in a poly-cistronic message (Adam et al. 1991 J .Virol. 65, 4985). However, the efficiency of an IRES is often low and tissue dependent making this strategy undesirable when one is seeking to maximise the efficiency of metabolic conversion of tyrosine through to dopamine. The present invention addresses these problems.

SUMMARY OF THE INVENTION

The present invention provides in one aspect a lentiviral vector capable of transducing a non-dividing or slowly-dividing cell, said vector comprising a lentiviral LTR-deleted vector. The vector can further comprise a nucleotide sequence encoding a polypeptide or protein of interest (POI), e.g., at least one nucleotide sequence of interest (NOI) encoding at least one POI. Advantageously, the NOI is operably linked to a promoter. If there is more than one NOI, there can be one promoter for driving expression, or a promoter for each NOI for driving expression. Thus, one or more NOI can be operably linked to one or more NOI. The vector can comprise a polynucleotide sequence, which encodes two or more POI, e.g., therapeutic POI, operably linked to a promoter, and the polynucleotide can encode a fusion POI. The invention thus can provide a way of expressing two therapeutic NOI from a single "chimeric" gene or polynucleotide. The vector may be for example an expression vector such as a plasmid, or it may be a retroviral vector particle comprising an RNA genome containing the nucleotide sequences as described herein.

In another aspect, the invention provides a method for producing a POI in a non-dividing or slowly-dividing cell, comprising transducing the cell with a lentiviral LTR-deleted vector and expressing the POI in the cell. In a preferred embodiment, the non-dividing cell is a neuron.

There are many uses for in vitro expressed POI. For instance, depending on the nature of the POI, the in vitro expressed POI can represent a protein that is purer than if the POI was isolated from its native environment, as it would be free from contaminants from that environment. Thus, such POI can be used in assays, to generate antibodies, e.g., for use in assays, as antigens or epitopes in immunological compositions, and as active agents in therapeutic, pharmaceutical or veterinary compositions, inter alia.

The invention further provides a target cell in vitro comprising a lentiviral LTR-deleted vector. In yet further aspects, the invention provides a DNA construct encoding the RNA genome for the retroviral vector particle; and a retroviral vector production system comprising a set of nucleic acid sequences encoding the components of the retroviral vector particle.

The invention further provides the use of retroviral vectors carrying the chimeric gene described herein, in gene therapy and in the preparation of a medicament for gene therapy; and a method of performing gene therapy on a target cell, which method comprises transducing the target cell with a lentiviral LTR-deleted vector comprising a nucleotide sequence encoding a POI, thus delivering the nucleotide sequence to the target cell. The invention further provides transduced target cells resulting from these methods and uses. The invention thus provides a gene delivery system for use in medicine.

The term "comprising" in this disclosure can mean "including" or can have the meaning commonly given to the term "comprising" in U.S. Patent Law.

Other aspects of the invention are described in or are obvious from (and within the ambit of the invention) the following disclosure.

BRIEF DESCRIPTION OF DRAWINGS

The following Detailed Description, given by way of example, but not intended to limit the invention to specific embodiments described, may be understood in conjunction with the accompanying drawings, incorporated herein by reference, in which:

FIG. 1 shows a general scheme for Lentiviral LTR-deleted (LLD) vectors which may be used with the present invention and which are employed in the Examples.

FIG. 2 shows a generalised HIV-based LLD vector genome as described in the Examples; Superscript H=HIV-derived sequence (could be from any lentivirus); Superscript M=MLV-derived sequence; 1V=Packaging site (including gag region); PBS=Second strand priming site; INTERNAL= Region containing genes, selectable markers, other promoters or RNA handling systems such as HIV RRE and Rev coding sequences.

FIG. 9 shows primers for use in the construction methods illustrated in FIGS. 7 and 8 and described in detail in the Examples. Lower case nucleotides denote rare codons in highly expressed genes in mammalian cells (Haas et al., 1996 Cur. Biol. 6, 315).

DETAILED DESCRIPTION OF THE INVENTION

Figure 3:
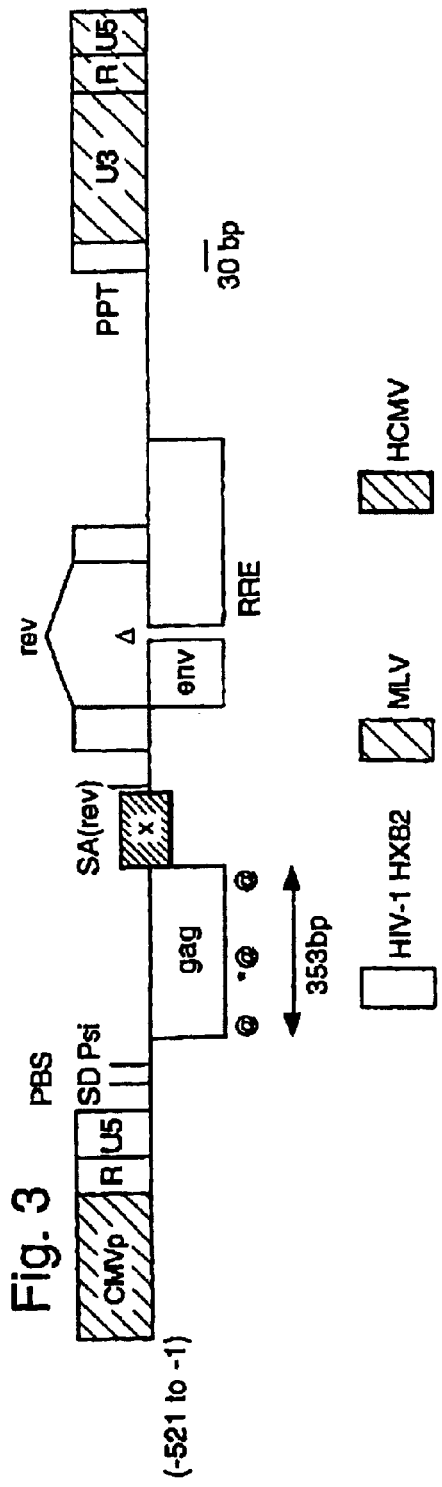
FIG. 3 shows a specific HIV-based LLD vector genome as described in the Examples. NIT vector genome (Inserts 3789 bp+backbone 2929 bp=6718 bp): HCMV promoter (−521 to −1) from pRV109; HIV sequences (552 to 1144; 5861 to 6403; 7621 to 9085) from HXB2; geonotype: gag−;pol−; env−;rev+;RRE; vif−;vpu−;vpr−;tat−;nef−; mutations; three point mutations to remove ATG (790, 834, 894) (@) a frameshift mutation by two base insertion (831) (*); a deletion between NdeI (6403) and BglII (7621) (Δ); polycloning site (X); XhoI-SalI-ClaI-EcoRV-EcoRI-PstI-SmaI-SmaI-BamHI-SpeI (underlined sites are unique); maximal insertion size into the polycloning site: 5997 bp; backbone: pBluescriptKS+

The lentivirus of the invention provides the ability to infect and transduce non-dividing and/or slowly-dividing cells. During the infection process, lentiviruses form a pre-integration complex in the target cell cytoplasm containing integrase, core proteins and the proviral DNA. The complex is able to pass across the nuclear membrane of the target cell, by means of signal sequences in the proteins. Other retroviruses either lack the proteins, or have the proteins but without the appropriate signal sequences. It is therefore expected to be possible in principle to introduce into retroviruses other than lentiviruses the ability to infect non-dividing or slowly-dividing cells.

To date, the most widely used retroviral vector systems for human gene therapy applications have used MLV. However, retroviral vector systems may also be based on other oncoretroviruses (the sub-group of retroviruses containing MLV), lentiviruses, or retroviruses from other sub-groups. Examples of lentiviruses are HIV, SIV, FIV, BLV, EIAV, CAEV and visna virus. Of these, HIV and SIV are presently best understood. However, preferred for use in gene therapy would be a non-immunodeficiency lentivirus because the immunodeficiency viruses inevitably bring with them safety considerations and prejudices. A range of retroviruses have already been split into packaging and vector components for retroviral vector particle production systems, including ASLV, SNV and RSV. It will be evident that a retroviral vector according to the invention need not be confined to the components of a particular retrovirus. The retroviral vector may comprise components derived from two or more different retroviruses, and may also comprise synthetic components. Vector components can be manipulated to obtain desired characteristics, such as target cell specificity.

The lentivirus group can be split into "primate" and "non-primate". Examples of primate lentiviruses include the human immunodeficiency virus (HIV), the causative agent of human acquired immunodeficiency syndrome (AIDS), and the simian immunodeficiency virus (SIV). The non-primate lentiviral group includes the prototype "slow virus" visna/maedi virus (VMV), as well as the related caprine arthritis-encephalitis virus (CAEV), equine infectious anaemia virus (EIAV) and the more recently described feline immunodeficiency virus (FIV) and bovine immunodeficiency virus (BIV).

Details on the genomic structure of some lentiviruses may be found in the art. By way of example, details on HIV and EIAV may be found from the NCBI Genbank database (i.e. Genome Accession Nos. AF033819 and AF033820 respectively), maintained by the National Institutes of Health. Details of HIV variants may also be found in the HIV databases maintained Los Alamos National Laboratory. Further details on EIAV can be found in U.S. Pat. No. 6,277,633, incorporated herein by reference.

Lentiviruses that are the subject of patents and patent publications and patent applications of Oxford Biomedica are advantageously employed in the practice of the invention.

During the process of infection, a retrovirus initially attaches to a specific cell surface receptor. On entry into the susceptible host cell, the retroviral RNA genome is then copied to DNA by the virally encoded reverse transcriptase which is carried inside the parent virus. This DNA is transported to the host cell nucleus where it subsequently integrates into the host genome. At this stage, it is typically referred to as the provirus. The provirus is stable in the host chromosome during cell division and is transcribed like other cellular genes. The provirus encodes the proteins and other factors required to make more virus, which can leave the cell by a process sometimes called "budding".

Each retroviral genome comprises genes called gag, pol and env which code for virion proteins and enzymes. These genes are flanked at both ends by regions called long terminal repeats (LTRs). The LTRs are responsible for proviral integration, and transcription. They also serve as enhancer-promoter sequences. In other words, the LTRs can control the expression of the viral genes. Encapsidation of the retroviral RNAs occurs by virtue of a psi sequence located at the 5' end of the viral genome.

The LTRs themselves are identical sequences that can be divided into three elements, which are called U3, R and U5. U3 is derived from the sequence unique to the 3' end of the RNA. R is derived from a sequence repeated at both ends of the RNA, and U5 is derived from the sequence unique to the 5'end of the RNA. The sizes of the three elements can vary considerably among different retroviruses.

For the viral genome, the site of transcription initiation is at the boundary between U3 and R in the left hand side LTR and the site of poly (A) addition (termination) is at the boundary between R and U5 in the right hand side LTR. U3 contains most of the transcriptional control elements of the provirus, which include the promoter and multiple enhancer sequences responsive to cellular and in some cases, viral transcriptional activator proteins. Some retroviruses have any one or more of the following genes that code for proteins that are involved in the regulation of gene expression: tat, rev, tax and rex.

With regard to the structural genes gag, pol and env themselves, gag encodes the internal structural protein of the virus. Gag protein is proteolytically processed into the mature proteins MA (matrix), CA (capsid) and NC (nucleocapsid). The pol gene encodes the reverse transcriptase (RT), which contains DNA polymerase, associated RNase H and integrase (IN), which mediate replication of the genome. The env gene encodes the surface (SU) glycoprotein and the transmembrane (TM) protein of the virion, which form a complex that interacts specifically with cellular receptor proteins. This interaction leads ultimately to infection by fusion of the viral membrane with the cell membrane.

Lentiviruses may also contain "additional" genes which code for proteins other than gag, pol and env. Examples of additional genes include in HIV, one or more of vif, vpr, vpx, vpu, tat, rev and nef. EIAV has, for example, the additional genes S2 and dUTPase.

Proteins encoded by additional genes serve various functions, some of which may be duplicative of a function provided by a cellular protein. In EIAV, for example, tat acts as a transcriptional activator of the viral LTR. It binds to a stable, stem-loop RNA secondary structure referred to as TAR. Rev regulates and co-ordinates the expression of viral genes through rev-response elements (RRE). The mechanisms of action of these two proteins are thought to be broadly similar to the analogous mechanisms in the primate viruses. The function of S2 is unknown. In addition, an EIAV protein, Ttm, has been identified that is encoded by the first exon of tat spliced to the env coding sequence at the start of the transmembrane protein.

For the production of retroviral vector particles, the vector RNA genome is expressed from a DNA construct encoding it, in a host cell. The components of the particles not encoded by the vector genome are provided in trans by additional nucleic acid sequences (the "packaging system", which usually includes either or both of the gag/pol and env genes) expressed in the host cell. The set of sequences required for the production of the retroviral vector particles may be introduced into the host cell by transient transfection, or they may be integrated into the host cell genome, or they may be provided in a mixture of ways. The techniques involved are known to those skilled in the art.

Certain retroviruses have special characteristics which may be useful in particular gene therapy applications. For example, the lentiviruses such as HIV are capable of infecting and transducing non-dividing and/or slowly-dividing cells because they have means for getting the proviral DNA across the nuclear membrane of target cells. This feature will be useful if it is desired to target non-dividing or slowly-dividing cell types in nucleic acid transfer. Such cell types include the neurons of the human brain, which are a potentially important target for gene therapy treatment of Parkinson's disease. A retroviral vector particle according to the invention may thus be derived from a lentivirus, at least to the extent that it is capable of delivering proviral DNA efficiently to a non-dividing or slowly-dividing cell.

The vector can comprise a non-lentiviral expression control element, which will usually be a promoter. This term includes known promoters, in part or in their entirety, which may be constitutively acting or may be inducible only under certain conditions e.g. in the presence of a regulatory protein. This enables expression of one or more NOI to be restricted e.g. to particular cell types or to cells in which a particular exogenous signal is present. For example, heavy metal induction of a NOI could be achieved by using components of the metallothionein promoter. Expression control by a steroid hormone may be another useful approach. Brain-specific, stem cell specific or tumour-specific gene expression signals might alternatively be used.

The non-lentiviral promoter replaces the lentiviral protein-dependent promoter function of the lentiviral 5' LTR. For HIV, this means that the 5' LTR is no longer responsive to the HIV Tat protein. Tat acts on the TAR region of R; in an HIV-based vector according to the invention functional TAR sequences are therefore absent in order to avoid reductions of translation by the TAR structure. Enhancer sequences contained in the HIV U3 regions are also preferably excluded. A straightforward way to achieve the desired vector LTRs is therefore to replace the lentiviral R regions and as far as possible the U3 regions, but leaving essential lentiviral sequences present such as a short sequence of the U3 region necessary for integration.

The invention is outlined in FIG. 1. The vector system is designated Lentiviral LTR-Deleted (LLD) vector. It comprises a DNA molecule in which a CMV or other high efficiency promoter is used to drive the expression of the vector RNA in a producer cell. This strategy is analogous to the HIT vector system (Soneoka et al., 1995 Nucl. Acids Res. 23, 628). The producer cell will have been engineered to produce compatible lentiviral structural proteins and enzymes. It will be, therefore, what is known as a vector packaging cell. The producer DNA can be used as an autonomous plasmid that either does or does not replicate or it can be integrated into the producer cell genome. All of these strategies are known in the field (Soneoka et al., 1995 Nucl. Acids Res. 23, 628; Miller and Rossman 1989 BioTech. 7, 980; Miller 1990 Hum. Gene Ther. 1, 5). The producer DNA for the vector genome may contain at least the following contiguous components: a high efficiency promoter; a non-lentiviral R region that either comes from another retrovirus or is completely synthetic; all or part of the lentiviral U5 region that contains sequences required for integration by the lentiviral integrase and sequences necessary for efficient reverse transcription; packaging signals that are recognized by the packaging components of the producer cell; an internal region that might contain one or more NOI, including therapeutic or reporter NOI or selectable markers and associated expression signals (in addition the internal region might contain components of systems for ensuring efficient RNA splicing and transport); a second strand primer site from the lentivirus; a short sequence of 30–100 nucleotides from the lentivirus U3 region that is required for efficient integration by the lentivirus integrase; a heterologous promoter that might confer tissue specificity of gene expression or regulation by an exogenous signal so that a NOI can be expressed appropriately; and an R region that is identical to the first R region together with transcription termination and polyadenylation signals required to produce a vector RNA with terminal R regions.

This producer DNA produces an RNA molecule that is packaged by the lentiviral packaging system. The resulting vector particles will deliver that RNA to a susceptible cell, the RNA will be converted to DNA by the lentiviral reverse transcriptase and it will be integrated into the cells genome by the lentiviral integrase. The resulting provirus will have the CMV promoter component of the producer DNA replaced by the short lentiviral sequence from the end of the lentiviral U3 region and the heterologous promoter that may confer tissue specific or regulated gene expression. Because the lentiviral R region has been entirely replaced, there are no inhibitory TAR sequences in the integrated vector genome.

As will be evident, in order to function as a vector, the lentiviral LTR-deleted vector according to the invention will need to have a reverse transcription system (compatible reverse transcriptase and primer binding sites) and an integration system (compatible integrase and integration sites) allowing conversion to the provirus and integration of the double-stranded DNA into the host cell genome. Usually these will include gag and pol proteins derived from the retrovirus. Additionally, the vector genome will need to contain a packaging signal. These systems and signals are described in more detail below in the Examples and will generally be provided by the retrovirus, on which the vector is based. That the vector particle according to the invention is "based on" a retrovirus means that it is derived from that retrovirus. The genome of the vector particle comprises components from that retrovirus as a backbone.

It will be evident also that, although the vector according to the invention is based on a particular retrovirus, this may be a genetically or otherwise (e.g. by specific choice of packaging cell system) altered version of the retrovirus. For example, portions of the retroviral genome not required for its ability to be packaged, undergo reverse transcription and integrate, can be excluded. Also, the vector system can be altered e.g. by using different env genes to alter the vector host range and cell types infected or transduced.

It may be advantageous to include further elements of the retrovirus on which the vector is based. For HIV this might include functional rev and RRE sequences, enabling efficient export of RRE-containing RNA transcripts of the vector genome from the nucleus to the cytoplasm of the target cell.

The selected NOI under the control of the exogenous promoter is or are chosen according to the effect sought to be achieved. For gene therapy purposes there will be at least one therapeutic NOI encoding a POI which is active against the condition it is desired to treat or prevent. Alternatively or additionally, there may be a selected NOI which acts as a marker by encoding a detectable product. A NOI may encode, for example, an anti-sense RNA, a ribozyme, a transdominant negative mutant of a target protein, a toxin, a conditional toxin, an antigen that induces antibodies or helper T-cells or cytotoxic T-cells, a single chain antibody or a tumour suppresser protein.

Preferably, the retroviral vector according to the invention is a single transcription unit vector, that is, the vector genome in DNA or RNA form is under the transcriptional control of no more than one vector promoter at any one time. In a preferred embodiment, this is achieved by locating the polynucleotide sequence according to the invention such that in the DNA form of the vector genome integrated into the target cell genome (the DNA provirus), it is under transcriptional control of the 5' LTR. There are alternative ways of achieving a single transcription unit vector, however. The vector genome could be designed as a self-inactivating vector (Yu et al., 1986 PNAS 83, 3194) in which part of the 3' U3 sequences are deleted so that the transduced vector genome has a non-functional 5' LTR promoter. The polynucleotide sequence according to the invention would be operably linked to an internal conditional promoter between the LTRs which could be activated once the vector has transduced a target cell. Activation of the promoter might be dependent upon cellular or external factors.

Although single transcription unit vectors are preferred, other vectors are not excluded. It may be useful for example to include a marker gene in the vector, operably linked to a different promoter which may be active simultaneously with the promoter responsible for transcription of the polynucleotide sequence encoding the fusion protein. A marker gene encoding a selectable marker may be useful for selecting successfully transfected packaging cells, or successfully transduced target cells. Marker genes encoding selectable markers may be for instance drug resistance genes or metabolic enzyme genes.

Where two or more NOI are present and under transcriptional control of the exogenous promoter, there may be an internal ribosome entry site (IRES) e.g. from picornaviral RNA, to allow both NOI to be separately translated from a single transcript. Retroviruses incorporating IRES sequences have been constructed by others.

A further NOI may also be present under the control of a separate promoter. Such a NOI may encode, for example, a selectable marker, or a further therapeutic agent which may be among the therapeutic agents listed herein. Expression of the NOI may be constitutive; in the case of a selectable marker this may be useful for selecting successfully transfected packaging cells, or for packaging cells which are producing particularly high titers of the retroviral vector particles. Alternatively or additionally, the selectable marker may be useful for selecting cells which have been successfully infected with the retroviral vector and have the provirus integrated into their own genome.

One way of performing gene therapy is to extract cells from a patient, infect the extracted cells with a retroviral vector and reintroduce the cells back into the patient. A selectable marker may be used to provide a means for enriching for infected or transduced cells or positively selecting for only those cells which have been infected or transduced, before reintroducing the cells into the patient. This procedure may increase the chances of success of the therapy. Selectable markers may be, for instance, drug resistance genes, metabolic enzyme genes, or any other selectable markers known in the art.

However, it will be evident that for many gene therapy applications of retroviral vectors, selection for expression of a marker gene may not be possible or necessary. Indeed expression of a selection marker, while convenient for in vitro studies, could be deleterious in vivo because of the inappropriate induction of cytotoxic T lymphocytes (CTLs) directed against the foreign marker protein. Also, it is possible that for in vivo applications, vectors without any internal promoters will be preferable. The presence of internal promoters can affect, for example, the transduction titres obtainable from a packaging cell line and the stability of the integrated vector. Thus, single transcription unit vectors, which may be bi-cistronic or poly-cistronic, coding for one or two or more NOI, may be the preferred vector designed for use in vivo.

It will be evident that the term "gene" is used loosely here, and includes any nucleic acid of interest coding for a desired polypeptide of interest. Usually, the NOI delivered by the vector according to the invention will be cDNAs.

The retroviral vector according to the invention may be constructed according to methods known in the art. It is desirable that the retroviral vector genome does not encode any unnecessary polypeptides, that is any polypeptides that are not required for achieving the effect the vector is designed for. In any case, the retroviral vector will be replication defective. Particular factors to be taken into consideration when constructing a retroviral vector include safety aspects and the avoidance of undesirable immune responses. Thus, it is necessary to exclude from the vector genome full length gag-pol or env coding regions, or preferably both. Preferably, the retroviral vector genome which will be inserted into the target cell in the form of a DNA provirus contains the minimum retroviral material necessary to function. This avoids both the possible reconstruction of infectious virus particles, and expression of unwanted virus proteins in the target cell which could otherwise evoke undesirable immune responses in the patient being treated.

The vector according to the invention will also be capable of infecting and transducing cells which are slowly-dividing, and which non-lentiviruses such as MLV would not be able to efficiently infect and transduce. Slowly-dividing cells divide once in about every three to four days. Mammalian non-dividing and slowly-dividing cells include brain cells, stem cells, terminally differentiated macrophages, lung epithelial cells and various other cell types. Also included are certain tumour cells. Although tumours contain rapidly dividing cells, some tumour cells especially those in the centre of the tumour, divide infrequently. The rate of cell division can easily be determined using proliferation assays known in the art.

DNA constructs encoding the vector genome described herein are preferably linked to a high efficiency promoter such as the CMV promoter. Other high efficiency promoters are known. This gives rise to a high level of expression of the vector RNA in the host cell producing the retroviral vector particles.

Suitable host or producer cells for use in the invention are well known in the art. Many retroviruses have already been split into replication defective genomes and packaging components. For those which have not the technology is available for doing so. The producer cell encodes the viral components not encoded by the vector genome such as the gag, pol and env proteins. The gag, pol and env genes may be introduced into the producer cell and stably integrated into the cell genome to give a packaging cell line. The retroviral vector genome is then introduced into the packaging cell line by transfection or transduction to create a stable cell line that has all of the DNA sequences required to produce a retroviral vector particle. Another approach is to introduce the different DNA sequences that are required to produce a retroviral vector particle e.g. the env coding sequence, the gag-pol coding sequence and the defective retroviral genome into the cell simultaneously by transient triple transfection (Landau & Littman 1992 J. Virol. 66, 5110; Soneoka et al. 1995).

The strategy according to the invention has several advantages in addition to those already described. Firstly, by making use of a non-lentiviral expression signal for a transcription unit it is possible to make this vector genome a single transcription unit genome for both production and expression in the transduced cell. This avoids the need for internal promoters. The unpredictable outcome of placing additional promoters within the retroviral LTR transcription unit is well documented (Bowtell et al., 1988 J .Virol. 62, 2464; Correll et al., 1994 Blood 84, 1812; Emerman and Temin 1984 Cell 39, 459; Ghattas et al., 1991 Mol. Cell. Biol. 11, 5848; Hantzopoulos et al., 1989 PNAS 86, 3519; Hatzoglou et al., 1991 J. Biol. Chem 266, 8416; Hatzoglou et al., 1988 J. Biol. Chem 263, 17798; Li et al., 1992 Hum. Gen. Ther. 3, 381; McLachlin et al., 1993 Virol. 195, 1; Overell et al., 1988 Mol. Cell Biol. 8, 1803; Scharfman et al., 1991 PNAS 88, 4626; Vile et al., 1994 Gene Ther 1, 307; Xu et al., 1989 Virol. 171, 331; Yee et al., 1987 PNAS 84, 5197). The factors involved appear to include the relative position and orientation of the two promoters, the nature of the promoters and the expressed nucleic acids and any selection procedures that may be adopted. The presence of internal promoters can affect both the transduction titers attainable from a packaging cell line and the stability of the integrated vector. Loss of gene expression following transduction can be caused both by provirus deletions and reversible epigenetic mechanisms of promoter shutdown. In addition, data from tissue culture studies can often have no bearing on the performance of the vectors in vivo. These considerations suggest that simple retroviral vectors containing a single LTR promoter are likely to be promising vectors for gene therapy (Correll et al., 1994 Blood 84, 1812). In addition, with the development of bi-cistronic vectors using only one promoter (Adam et al., 1991 J .Virol 65,4985) it will also be possible to produce single transcription unit vectors coding for two or more NOI, with correspondingly greater efficacy.

The second advantage of removing the HIV expression signals within the U3 and R regions is that these signals are subject to a number of external influences on their activity. It is known that the HIV promoter can be activated by a variety of agents such as UV, stress, other viruses etc. (Peterlin 1992 in Human Retroviruses ed. Cullen. IRL Press) which makes the transcriptional status of the vector genome difficult to control. Removal of these sequences will ensure greater control over the nucleotide to be expressed.

In one embodiment, one or more NOI of interest is or are chosen according to the effect sought to be achieved. The fusion protein has or is capable of having the desired activity of the therapeutic gene products. The product encoded by one or more of the NOI may be an enzyme. The fusion protein may thus display the activity of one or more enzymes. Where the NOI encode two different enzymes, the resulting fusion protein is a bifunctional enzyme. In the specific example described herein, the fusion protein comprises the enzymes tyrosine hydroxylase and DOPA dehydroxylase having enzyme activities as described above.

Preferably the NOI are linked by a sequence encoding a flexible linker. A suitable linker may comprise amino acid repeats such as glycine-serine repeats. The purpose of the linker is to allow the correct formation and/or functioning of the POI. It must be sufficiently flexible and sufficiently long to achieve that purpose. Where the NOI encode two different enzymes, the linker needs to be chosen to allow the functioning of both of the enzymes. The coding sequence of the flexible linker may be chosen such that it encourages translational pausing and therefore independent folding of the protein products of the NOI.

A person skilled in the art will be able to design suitable linkers in accordance with the invention. Some specific examples of suitable linkers are given below; it will be evident that the invention is not limited to these particular linkers.

1. (Gly-Gly-Gly-Gly-Ser)3 (SEQ ID NO:21) as described in Somia et al., 1993 PNAS 90, 7889.

2. (Gly-Gly-Gly-Gly-Ser)5, (SEQ ID NO:22) a novel linker.

3. (Asn-Phe-Ile-Arg-Gly-Arg-Glu-Asp-Leu-Leu-Glu-Lys-Ile-Ile-Arg-Gln-Lys-Gly-Ser-Ser-Asn) (SEQ ID NO:23) from HSF-1 of yeast, see Wiederrecht et al., 1988 Cell 54, 841.

4. (Asn-Leu-Ser-Ser-Asp-Ser-Ser-Leu-Ser-Ser-Pro-Ser-Ala-Leu-Asn-Ser-Pro-Gly-Ile-Glu-Gly-Leu-Ser) (SEQ ID NO:24) from POU-specific OCT-1, see Dekker et al., 1993 Nature 362, 852 and Sturm et al., 1988 Genes and Dev. 2, 1582.

5. (Gln-Gly-Ala-Thr-Phe-Ala-Leu-Arg-Gly-Asp-Asn-Pro-GlnGly) (SEQ ID NO:25) from RGD-containing Laminin peptide, see Aumailly et al., 1990 FEBS Lett. 262, 82.

6. (Ser-Gly-Gly-Gly-Glu-Ile-Leu-Asp-Val-Pro-Ser-Thr-Gly-GlySer-Ser-Pro-Gly) (SEQ ID NO:26) from LDV-containing linker, see Wickham et al., Gene Therapy 1995 2, 750.

In addition to gene therapy, the invention has several other useful applications. The alteration of gene expression, by upregulating or downregulating the production of gene products can be accomplished using the vectors of the invention. The vectors of the invention can also be employed in vitro to produce therapeutic proteins, to express selectable markers, or for other expression assays. Examples of proteins that may be expressed using the vectors of the invention include, but are not limited to, Factor VIII, Factor IX, erythropoietin, alpha-1 antitrypsin, calcitonin, glucocerebrosidase, growth hormone, low density lipoprotein (LDL) receptor, apolipoproteins (e.g. apolipoprotein E or apolipoprotein A-I), interleukins, interleukin receptors and antagonists, insulin, globin, immunoglobulins, catalytic antibodies, superoxide dismutase, immune responder modifiers, parathyroid hormone, interferons, growth factors, including insulin-like growth factors and nerve growth factors, tissue plasminogen activators, colony stimulating factors, and variants of these proteins.

In the particular embodiment described herein, the invention addresses the problems of the prior art by providing a single fusion gene that expresses a fusion protein composed of TH and DD. The single gene encodes a single protein with both enzyme activities. This permits the construction of a simple single transcription unit retroviral vector that expresses both enzyme activities efficiently. The fusion gene is designed such that the enzymes are linked via a flexible linker, the coding sequence of which has a short cluster of infrequently used codons (Haas et al., 1996 Curr. Biol. 6, 315) to encourage translational pausing and, therefore, independent folding of the two domains of the new bifunctional enzyme. Two different types of fusion gene were made. In the first the order of the enzyme activities is TH-DD and in the other it is DD-TH. Both types are made because they may have different advantages and properties under different conditions. Human tyrosine hydroxylase is encoded by a single gene which is alternatively spliced to create four types of TH that differ towards their amino terminus (Grima et al., 1987 Nature 326, 707; Kaneda et al., 1987 BBRC 146, 971). However, identical primers can be used to isolate all four cDNAs by PCR as the termini are the same.

The following examples are provided as a further description of the invention, and to illustrate but not limit the invention.

EXAMPLES

Example 1

An HIV-Based LLD Vector with the MLV U3 Promoter and MLV R Regions

Lentiviral vectors are particularly useful for gene transfer to non-dividing cells. Amongst many important non-dividing target cells are the neurons of the human brain. These cells might be target cells for the delivery of thdd or ddth cells for the treatment of Parkinson's disease. This Example describes the construction of an HIV based vector which will deliver and express thdd or ddth genes, for example.

Figure 4:
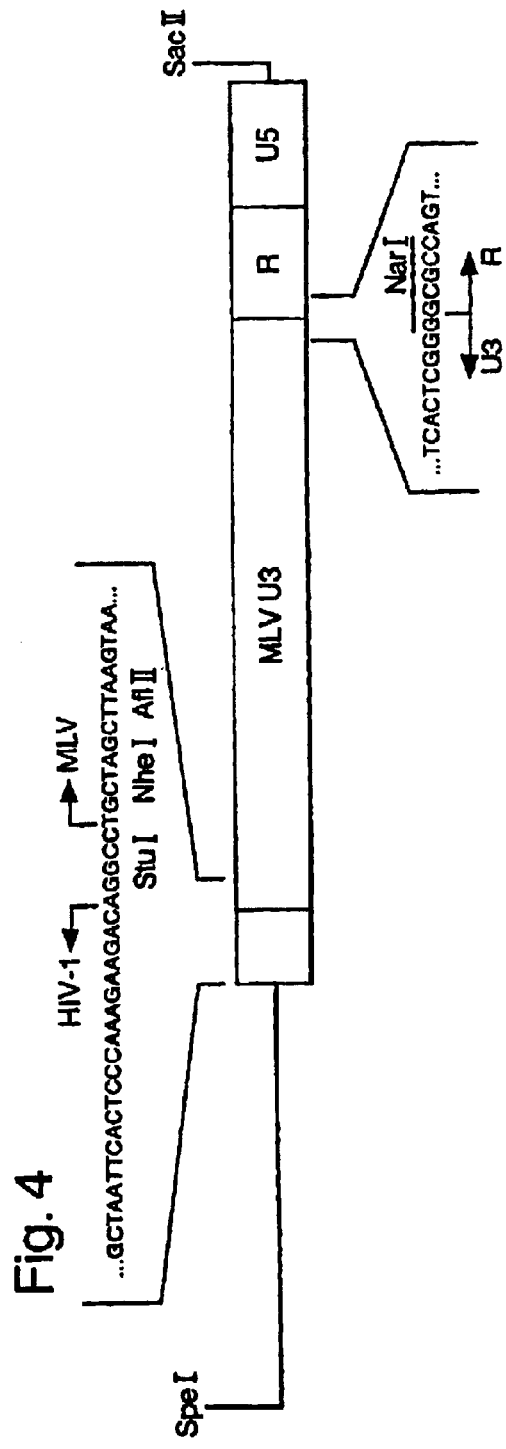
FIG. 4 shows in detail the structure of the 3' LTR for the vector in FIG. 3. SEQ ID NOs:27 and 28 are shown.

The structure of a general HIV LLD vector system is shown in FIG. 2. This example is shown in FIGS. 3 and 4. It is constructed as follows. the minimal requirements for HIV reverse transcription are the primer binding site (PBS) to initiate the negative strand DNA synthesis, the polypurine tract (PPT) to initiate the positive DNA synthesis, and identical 5' and 3' R sequences to allow the first template switch. The incorporation of the PBS and PPT from HIV-1 into the vector and the R sequences from MLV into both LTRs is therefore required. As secondary structure within the 5' U5 region might be important for reverse transcription, the U5 region in the 5' LTR is from HIV-1. For the U5 region at the 3' LTR, the U5 from HIV-1 was used to make sure correct termination of transcription occurred at the R-U5 border. However, any termination signals could be used. For efficient integration, 30 nucleotides at the 5' end of the HIV-1 U3 at the 3' LTR were incorporated.

In order for the MLV U3 element to appear in the 5' LTR after reverse transcription, it must be in the 3' LTR of the viral RNA. The whole MLV U3 except 30 bps of the 5' end replaced the HIV-1 U3. The 3' LTR of the vector was designed to contain several convenient restriction sites, so that the MLV U3 can be easily replaced by other heterologous promoters (FIG. 4). Any heterologous promoters will be amplified by PCR with primers containing StuI and NarI sites at each end and will be used to replace the MLV U3. Not only StuI but also NheI and AfIII may be used at the 5' end of the promoter cassettes. NarI(GGCGCC) is located on the junction between the promoter and R, so that the transcription start site from the heterologous promoter can be preserved. The MLV U3 sequences between XbaI and NarI contains the basic promoter elements including TATA box, GC box, and CAAT box. Therefore the MLV enhancer can be replaced by any other enhancers as a StuI (or NheI or AfIII)-XbaI cassettes.

For efficient packaging 353 nucleotides of gag is known to be sufficient (Srinivasakumar et al., 1996 CSH Retrovirus Meeting abstract). The 353 nucleotides of gag sequences corresponds to the sequences from 790 to 1144, within this three ATG's (790, 834, 894) were removed by mutation. In addition a polycloning site is located downstream of gag.

In order to achieve efficient export of RNA species encoded by HIV genome, rev and RRE, are required. They are included in the LLD vector and correspond to sequences 5861 to 6403 and 7621 to 9085 from is HIV-1 (HXB2). Tat coding sequence is not present in the vector.

Details of Construction of the Producer DNA:

A. 5' Structure (All HIV-1 Coordinates are from HXB from the Los Alamos Sequence Database and MoMLV Sequences are from Shinnick et al. 1981 Nature 293. 543)

The 5' half of the vector contains the hybrid 5' LTR (CMV promoter-MLV R-HIV-1 U5), HIV-1 PBS, and HIV-1 packaging signal. This will be constructed by recombination PCR. One of the templates for the PCR, pHIVdge2, is an HIV-1 proviral DNA which has a mutation created by filling-in and religation at the ClaI site (831) and a deletion between NdeI(6403) and BglII(7621). The junction between MLV R and HIV-1 U5 is created by two primary PCR reactions (using the primer NIT1 and NIT2; NIT3 and NIT4) and a secondary PCR reaction (using the primers NIT1 and NIT4). The PCR product is inserted into pBluesriptKS+ (STRATAGEN) at KpnI and XhoI site (Construct A1). In order to mutate three ATGs in the gag region, the primers contain mutated codons.

| | | |
|---|---|---|
| NIT1: | 5'-ccgggtacccgtattcccaataaagcctcttgctgtttgca-3' | (SEQ ID NO:1) |
| NIT2: | 5'-ctacgatctaattctccccgcttaatactgacgctctcgcacctatctc-3' | (SEQ ID NO:2) |

-continued

```
NIT3:    5'-gcggggagaattagatcgtagggaaaaaattcggttaaggccaggggaaagaaaaaatataaatt    (SEQ ID NO:3)
         aaaacatatagtttggg-3'

NIT4:    5'-gaattctcgaggcgtgctgtgcttttttctatc-3'                                 (SEQ ID NO:4)
```

The CMV promoter—MLV R fragment is amplified by PCR from pRV109 (Soneoka et al., 1995 Nucl. Acids Res. 23, 628) to contain KpnI sites at both ends using the PCR primers NIT5 and NIT6 and inserted into construct A1 to produce construct A2.

```
                                                                                (SEQ ID NO:5)
NIT5:    5'-gtaggtacccgttacataacttacggtaaatg-3'

(SEQ ID NO:6)
NIT6:    5'-agaggctttattgggaatacg-3'
```

B. 3' Structure

The 3' half of the vector genome includes the HIV-1 rev coding region and RRE, PPT, 36 by of 5' end of HIV-1 U3, and the whole MLV LTR except 30 by of 5'end. The sequences (5861–6000) are PCR amplified from pHIVdge2 (using NIT7 and NIT8) and are subcloned into pSP64 (PROMEGA) at BamHI and SacI site (Construct B1).

```
                                                                                (SEQ ID NO:7)
NIT7:    5'-cacggatccactagttggaagcatccaggaagtcagc-3'

(SEQ ID NO:8)
NIT8:    5'-ctctgactgttctgatgagc-3'
```

The SacI-SacI fragment (6000–6403 and 7621–9572) from pHIVdge2 is inserted into the above construct to produce construct B2. Finally the HIV-1-MLV hybrid LTR will be created by two primary PCRs (using NIT9 and NIT10 with pHIVdge2 as the template; NIT11 and NIT12 with pLXSN (Accession number M28248; Miller et al., 1989) as the template) and one secondary PCR reaction (using NIT9 and NIT12). The PCR product will be inserted at the XhoI and EcoRI sites in Construct B2 to produce Construct B3.

```
NIT9:    5'-gagcagcatctcgagacctgg-3'                                             (SEQ ID NO:9)

NIT10:   5'-tggcgttacttaagctagcaggcctgtcttctttgggagtgttttagc-3'                  (SEQ ID NO:10)

NIT11:   5'-cccaaagaagacaggcctgctagcttaagtaacgccatttttcc-3'                      (SEQ ID NO:11)

NIT12:   5'-cctgaattccgcggaatgaaagaccccgctgacg-3'                                (SEQ ID NO:12)
```

C. Complete Vector

The two halves of the vector are combined by inserting the SpeI-SacII fragment from construct B3 into construct A2. The resulting construct, C1, possesses a poly-cloning site; XhoI-SalI-ClaI-HindIII-EcoRV-EcoRI-PstI-SmaI-BamHI-SpeI(underlined sites are unique in the vector). This plasmid is designated pLLD1 and the retroviral vector that it produces is LLD1.

The β-galactosidase gene was then taken from pSP72-lacZ (XhoI-BamHI) and inserted into the construct C1 at SalI and BamHI to produce LLD1-lacZ. This was used to transfect 293T cells together with plasmids providing the HIV gag and pol components (pRV664, FIG. 5) and either a plasmid expressing gp160 from HIV (pRV438 or pSynp160 mn, FIG. 5) or a plasmid expressing the VSVG protein (pRV67, FIG. 5). Any plasmids encoding the same proteins would work equally well. The resulting virus that is produced transduced the lacZ gene to CD4+ Hela cells in the case of virus containing gp160 and to CD4− Hela cells in the case of the VSVG bearing virus. In addition the VSVG bearing virus delivers lacZ to post-mitotic neurones. In each case the expression of the lacZ gene is high, as determined by Xgal staining, and independent of Tat.

Figure 5:
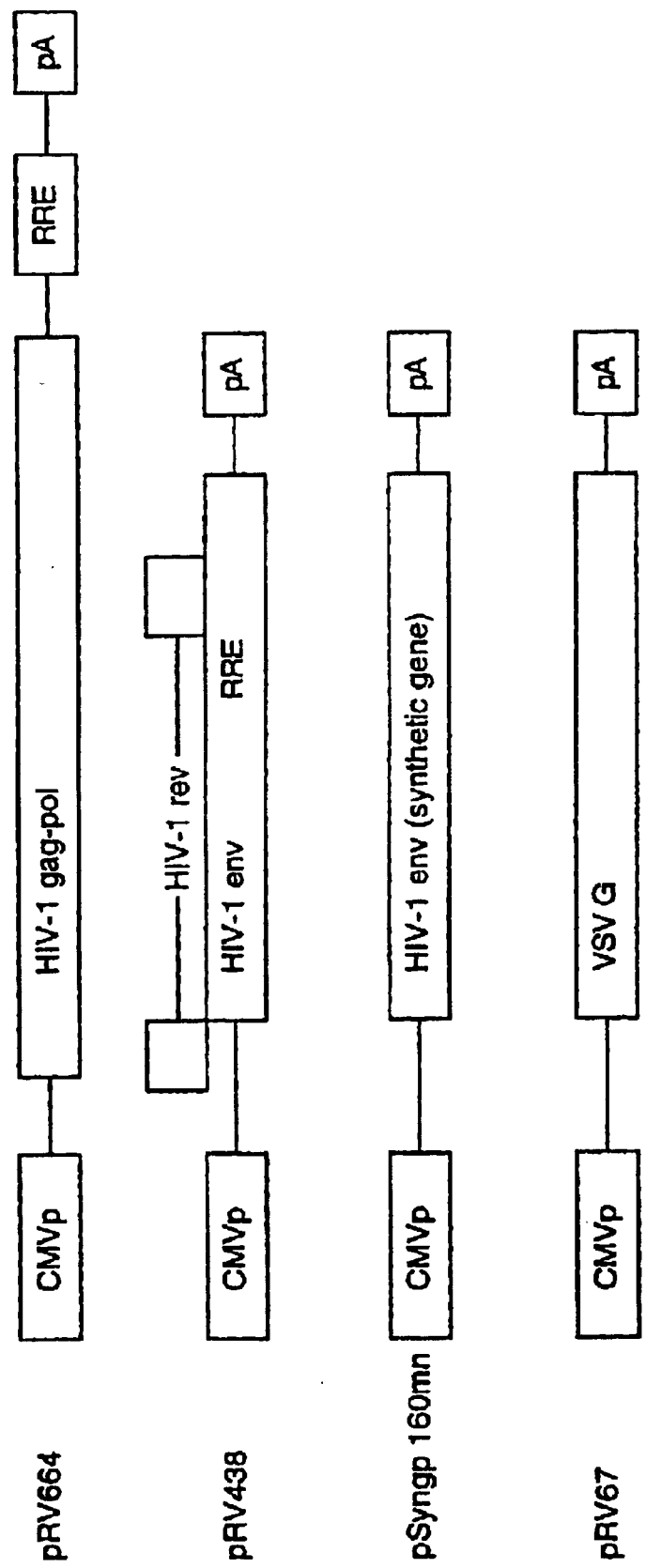
FIG. 5 shows a schematic diagram of packaging components suitable for use with the vector genome shown in FIGS. 1 to 3. pRV664 encodes HIV-1 HXB2 gagpol (637–5748) and contains RRE (77208054) and its backbone is pCI-neo (PROMEGA). pRV438 possesses both rev and env from HXB2 (5955–8902) in pSA91 which is a mammalian expression plasmid with CMC promoter. pSyngp 160 mn (from B. Seed) is an expression plasmid for HIV-1 MN envelope which was modified to have the optimized codon usage in mammalian cells. pRV67 is a VSV G expression plasmid in pSA91.
Figure 6:
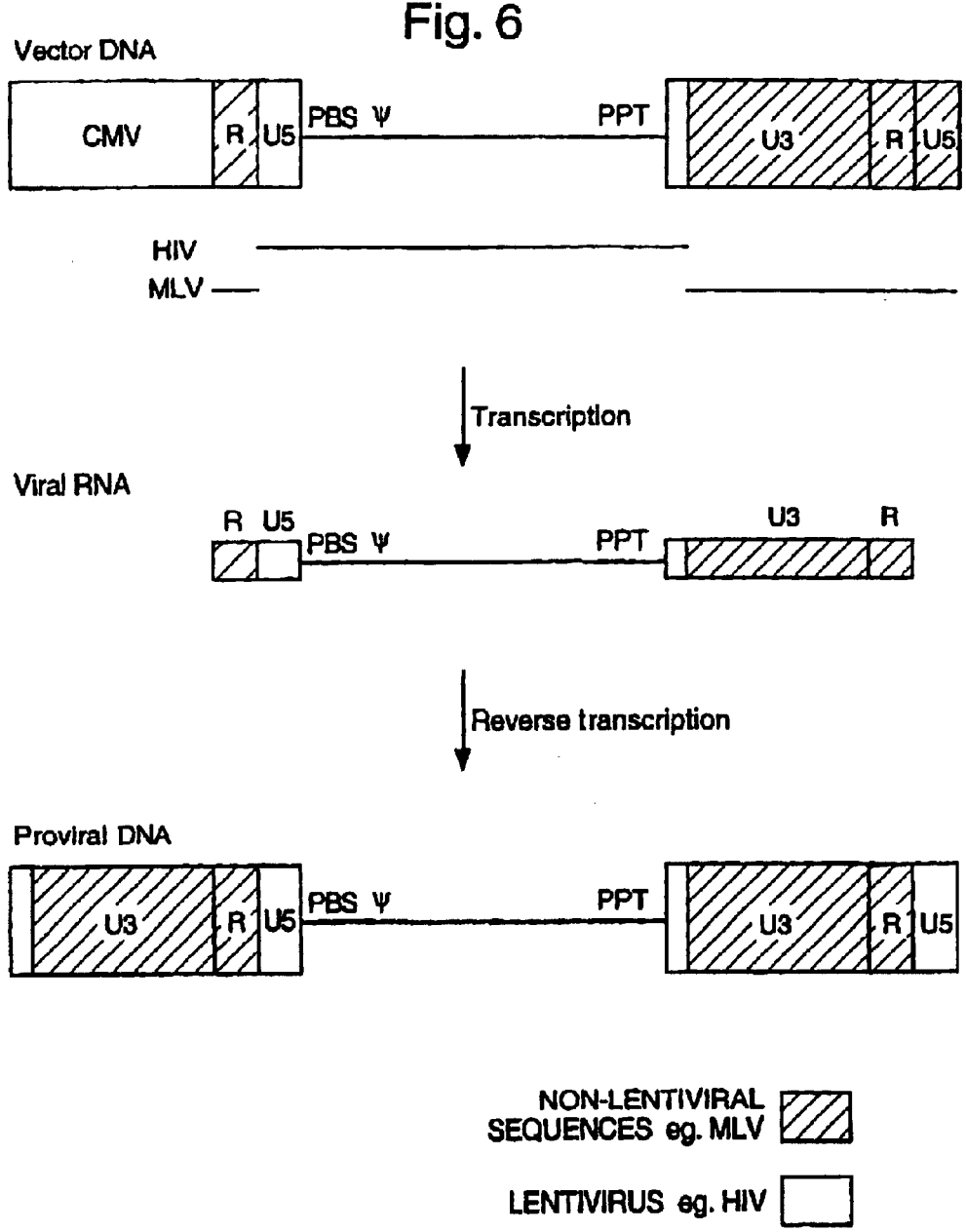
FIG. 6 further shows the principle of vectors according to this invention.

Alternatively, ddth1 is used to illustrate the principle of a fusion construct, but any of the fusion genes could be used. Plasmid pX1 is cut with HincII and SpeI and the fragment purified. This is then inserted into LLD1 cut with EcoRV and SpeI to create pLLD1:thdd1. When this is transfected into a packaging cell line (suitable packaging components are shown in FIG. 5) and viral vector particles produced, those vector particles deliver the thdd gene to the recipient cells where the fusion enzymes are expressed. Such a retroviral vector system is useful for the treatment of Parkinson's disease by gene therapy.

Example 2

Other LLD Vectors

Systems similar to that described in Example 1 can be produced from other lentiviruses. These systems avoid using HIV, with its associated perceived risks as a gene delivery system. For example constructions could be designed using sequence information from FIV (Talbott et al., 1989 PNAS 86, 5743), EIAV (Payne et al., 1994 J. Gen. Virol. 75, 425), Visna virus (Sonigo et al., 1985 Cell 42, 369; Querat et al., 1990 Virology 175, 434), BIV (Garvey et al., 1990 Virology 175, 391), CAEV (Saltarelli et al., 1990 Virology 179, 347) and SIV (Los Alamos sequence database).

Example 3

Figure 7:
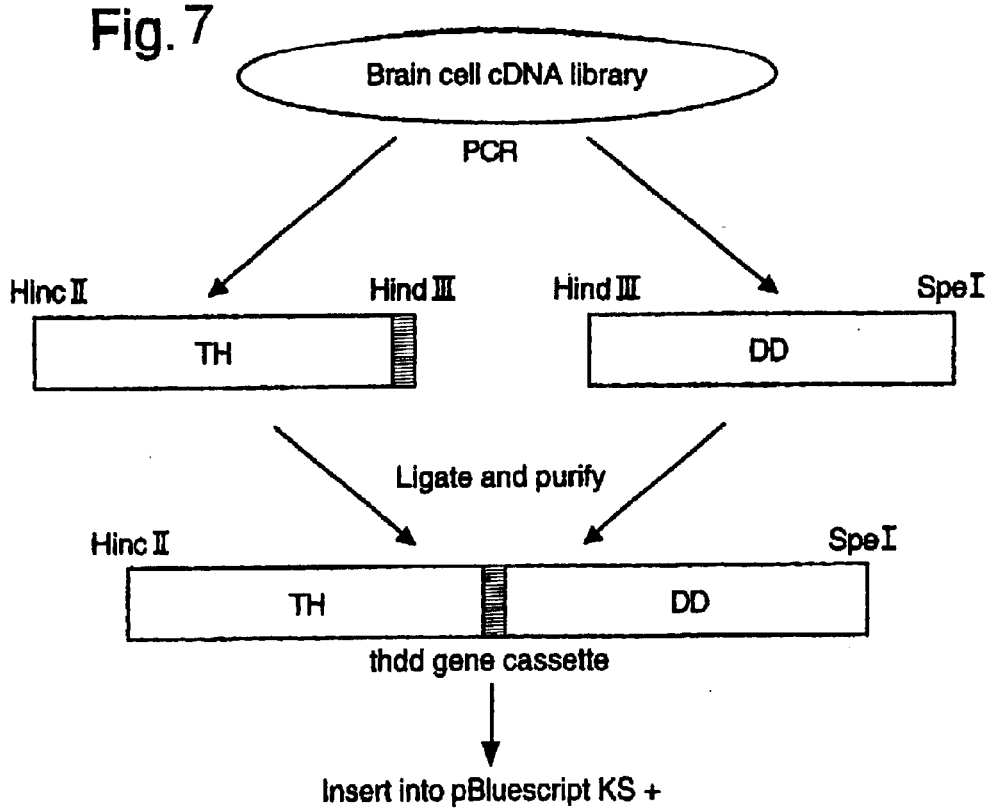
FIG. 7 shows simplified directions for construction of polynucleotide sequences according to the invention, encoding TH-DD fusion proteins.

Construction of TH-DD Fusion Genes Designated thdd1-4 (FIG. 7)

A human brain Substantia nigra cDNA library (Clontech. HI-3009a & b) is used as template DNA in a PCR amplification of the TH and DD cDNAs. The primers are shown in FIG. 9. In the case of the four TH cDNAs representing the HTH-1 to HTH-4 genes (Grima et al.; Kaneda et al.), they are all treated in the same way from a pool of PCR products and then identified after cloning and sequencing. The TH PCR products are produced from linkers containing a HincII site at the 5' end of the nucleic acid and a flexible linker and HindIII site at the 3' end. The flexible linker amino acid sequence is (Gly$_4$-Ser)$_3$, a sequence often used to link the two chains of an antibody to produce an scFv (e.g. Somia et al., 1995 PNAS 92, 7570). The human DD PCR product was designed to have a HindIII site at the 5' end and a SpeI site at the 3' end. The two fragment are ligated and the ligated products of the correct size (2.98 kb, 2.99 kb, 3.06 kb and 3.07 kb for the four variants) are purified from an agarose gel. The purified fragments are then inserted into pBLUEscriptKS+ using HincII and SpeI. This ligation mixture is used to transform E.coli (XL2-Blue ex. Stratagene 200249) and clones were used to prepare DNA which is then sequenced to ensure that the genes are intact and to identify HTH1-4. Plasmids containing fragments encoding the four different HTH coding sequences fused to DD are designated pthdd1-4. The the HincII-SpeI fragments from these plasmids are then inserted into the mammalian expression vector pC1-neo (Promega E1841). This is achieved by cutting pC1-neo with XhoI and SmaI and cutting the pBluescriptKS+ derived plasmids with SpeI and blunt ending and then cutting with XhoI. The cut products are then ligated together and correct plasmids checked by minipreps. The pC1-neo plasmids containing the fusion genes are designated pC1thdd1-4. These are then used to transiently transfect 293T cells which are then assayed for TH and DD by the methods of Waymire et al. (1971) (Anal. Biochem. 43, 588) and the method described in Anal. Biochem. (1984139, 73). In each case significantly increased levels of TH and DD are seen compared with control cells transfected only with pC1-neo. This demonstrates that the fusion genes expresses fusion proteins with both activities.

Example 4

Figure 8:
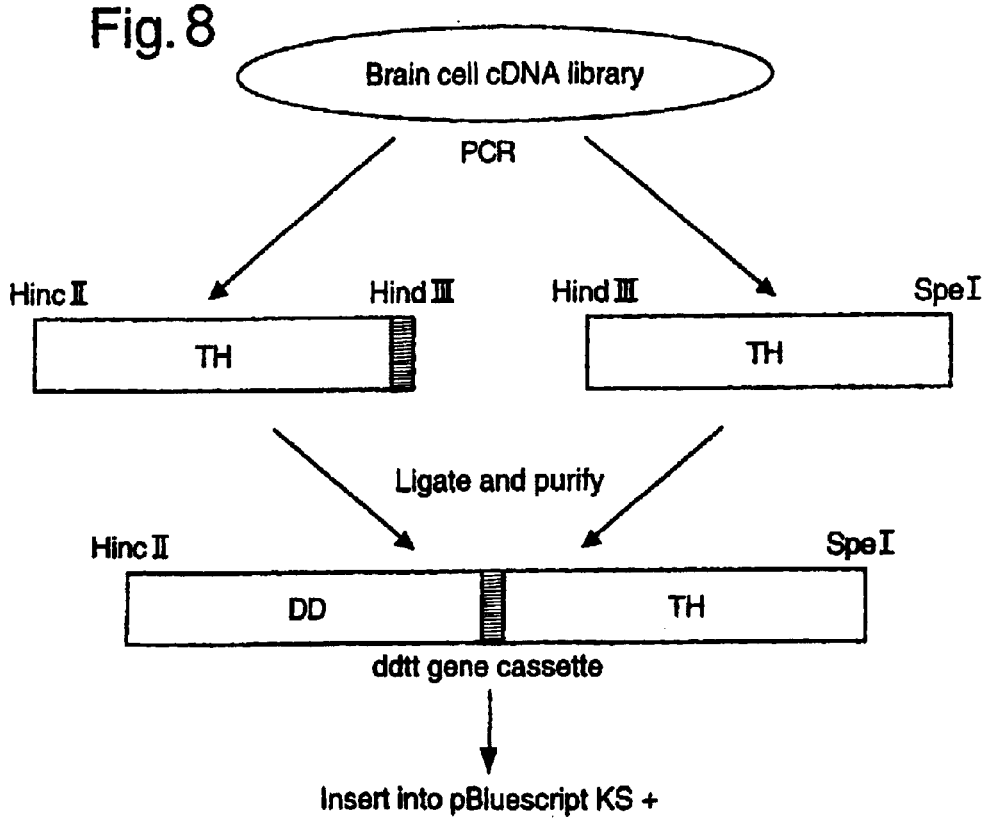
FIG. 8 shows simplified directions for construction of polynucleotide sequences according to the invention, encoding DD-TH fusion proteins.

Construction of DD-TH Fusion Genes Designated ddth1-4 (FIG. 8)

The construction of these genes is identical to that of Example 3 but the DD and TH coding sequences are in reciprocal locations. Similarly dual enzyme activities are encoded by the ddth1-4 genes.

Example 5

Construction of a Retroviral Vector Expressing a thdd Gene is a Single Transcription Unit Configuration The thdd and ddth genes are useful for the gene therapy of Parkinson's disease. They can be used in a wide range of vectors but they are particularly suited to single transcription unit retroviral vectors. An example of such a vector is produced as follows: Starting with pLNSX (Miller) a polylinker is inserted into the vector. Briefly, a SspI/HindIII fragment, containing the polylinker from pBluescriptKS+ is inserted into pLNSX cut with SspI and HindIII. The resulting plasmid is known as pMLD1. Plasmid, pX1, for example, is then cut with SpeI and then the ends filled in with DNA polymerase. The plasmid is then cut again with XhoI. The resulting thdd fragment is then inserted into pMLD1 cut with XhoI and ClaI (blunt-ended) to produce the resulting molecule pMLD1:thdd1. When this plasmid is used to transfect a packaging cell line retroviral vectors are produced which transduce susceptible cells with the thdd gene in a single transcription unit configuration. In this case the gene is expressed from the MLV LTR promoter but any promoter inserted into the 5' LTR via a U3 replacement or similar strategy would be equally effective.

Having thus described in detail preferred embodiments of the present invention, it is to be understood that the invention defined by the appended claims is not to be limited to particular details set forth in the above description, as many apparent variations thereof are possible without departing from the spirit or scope of the present invention. Modifications and variations of the method and apparatuses described herein will be obvious to those skilled in the art, and are intended to be encompassed by the following claims.

We claim:

1. A lentiviral vector particle capable of transducing a non-dividing or slowly-dividing cell, said vector particle comprising a lentiviral LTR-deleted (LCD) vector, wherein the LLD vector comprises sequences sufficient for reverse transcription and integration, and wherein, upon transduction, the LLD vector comprises a non-functional lentiviral 5' LTR promoter.

2. The vector particle according to claim 1, further comprising a nucleotide sequence of interest (NOI).

3. A method for producing a protein of interest in a non-dividing or slowly-dividing cell, comprising the steps of:

a) transducing the cell with the vector particle according to claim 2, wherein the NOI encodes a protein of interest; and b) expressing the protein of interest in the cell.

4. The method according to claim 3, wherein the non-dividing cell is a neuron.

5. A target cell in vitro comprising the vector particle of claim 1.

6. A target cell in vitro comprising the vector particle of claim 2.

* * * * *

UNITED STATES PATENT AND TRADEMARK OFFICE
CERTIFICATE OF CORRECTION

PATENT NO. : 6,924,123 B2 Page 1 of 1
DATED : August 2, 2005
INVENTOR(S) : Alan John Kingsman and Susan Mary Kingsman It is certified that error appears in the above-identified patent and that said Letters Patent is hereby corrected as shown below:

<u>Column 27,</u>
Line 36, "(LCD)" should read -- (LLD) --.

Signed and Sealed this

Thirtieth Day of May, 2006

JON W. DUDAS
*Director of the United States Patent and Trademark Office*

SEQUENCE LISTING

<160> NUMBER OF SEQ ID NOS: 28

<210> SEQ ID NO 1
<211> LENGTH: 41
<212> TYPE: DNA
<213> ORGANISM: Unknown
<220> FEATURE:
<223> OTHER INFORMATION: Primer NIT1 used in PCR reaction to create
      junction between MLV R and HIV-1 U5

<400> SEQUENCE: 1
ccgggtaccc gtattcccaa taaagcctct tgctgtttgc a                          41

<210> SEQ ID NO 2
<211> LENGTH: 50
<212> TYPE: DNA
<213> ORGANISM: Unknown
<220> FEATURE:
<223> OTHER INFORMATION: Primer NIT2 used in PCR reaction to create
      junction between MLV R and HIV-1 U5

<400> SEQUENCE: 2
ctacgatcta attctcccc gcttaatact gacgctctcg cacctatctc                  50

```
<210> SEQ ID NO 3
<211> LENGTH: 84
<212> TYPE: DNA
<213> ORGANISM: Unknown
<220> FEATURE:
<223> OTHER INFORMATION: Primer NIT3 used in PCR reaction to create
      junction between MLV R and HIV-1 U5

<400> SEQUENCE: 3
gcgggggaga attagatcgt agggaaaaaa ttcggttaag gccaggggga aagaaaaat      60 ataaattaaa acatatagtt tggg                                            84

<210> SEQ ID NO 4
<211> LENGTH: 33
<212> TYPE: DNA
<213> ORGANISM: Unknown
<220> FEATURE:
<223> OTHER INFORMATION: Primer NIT4 used in PCR reaction to create
      junction between MLV R and HIV-1 U5

<400> SEQUENCE: 4
gaattctcga ggcgtgctgt gctttttcct atc                                  33

<210> SEQ ID NO 5
<211> LENGTH: 32
<212> TYPE: DNA
<213> ORGANISM: Unknown
<220> FEATURE:
<223> OTHER INFORMATION: PCR primer NIT5 used in amplification of CMV
      promoter

<400> SEQUENCE: 5
gtaggtaccc gttacataac ttacggtaaa tg                                   32

<210> SEQ ID NO 6
<211> LENGTH: 21
<212> TYPE: DNA
<213> ORGANISM: Unknown
<220> FEATURE:
<223> OTHER INFORMATION: PCR primer NIT6 used in amplification of CMV
      promoter

<400> SEQUENCE: 6
agaggcttta ttgggaatac g                                               21

<210> SEQ ID NO 7
<211> LENGTH: 37
<212> TYPE: DNA
<213> ORGANISM: Unknown
<220> FEATURE:
<223> OTHER INFORMATION: PCR primer NIT7 used in amplification of
      pHIVdge2

<400> SEQUENCE: 7
cacggatcca ctagttggaa gcatccagga agtcagc                              37

<210> SEQ ID NO 8
<211> LENGTH: 20
<212> TYPE: DNA
<213> ORGANISM: Unknown
<220> FEATURE:
<223> OTHER INFORMATION: PCR primer NIT8 used in amplification of
      pHIVdge2

<400> SEQUENCE: 8
ctctgactgt tctgatgagc                                                 20
```

```
<210> SEQ ID NO 9
<211> LENGTH: 21
<212> TYPE: DNA
<213> ORGANISM: Unknown
<220> FEATURE:
<223> OTHER INFORMATION: PCR primer NIT9 used to prepare HIV-1-MLV
      hybrid LTR

<400> SEQUENCE: 9
gagcagcatc tcgagacctg g                                               21

<210> SEQ ID NO 10
<211> LENGTH: 48
<212> TYPE: DNA
<213> ORGANISM: Unknown
<220> FEATURE:
<223> OTHER INFORMATION: PCR primer NIT10 used to prepare HIV-1-MLV
      hybrid LTR

<400> SEQUENCE: 10
tggcgttact taagctagca ggcctgtctt ctttgggagt gttttagc                  48

<210> SEQ ID NO 11
<211> LENGTH: 44
<212> TYPE: DNA
<213> ORGANISM: Unknown
<220> FEATURE:
<223> OTHER INFORMATION: PCR primer NIT11 used to prepare HIV-1-MLV
      hybrid LTR

<400> SEQUENCE: 11
cccaaagaag acaggcctgc tagcttaagt aacgccattt ttcc                      44

<210> SEQ ID NO 12
<211> LENGTH: 35
<212> TYPE: DNA
<213> ORGANISM: Unknown
<220> FEATURE:
<223> OTHER INFORMATION: PCR primer NIT12 used to prepare HIV-1-MLV
      hybrid LTR

<400> SEQUENCE: 12
cctgaattcc gcggaatgaa agaccccgc tgacg                                 35

<210> SEQ ID NO 13
<211> LENGTH: 33
<212> TYPE: DNA
<213> ORGANISM: Unknown
<220> FEATURE:
<223> OTHER INFORMATION: TH5-1 mammalian primer used to amplify the
      tyrosine hydroxyase (TH) gene from cDNA library

<400> SEQUENCE: 13
cacagtcgac catgcccacc cccgacgcca cca                                  33

<210> SEQ ID NO 14
<211> LENGTH: 77
<212> TYPE: DNA
<213> ORGANISM: Unknown
<220> FEATURE:
<223> OTHER INFORMATION: TH3-1 mammalian primer used to amplify the
      tyrosine hydroxyase (TH) gene from cDNA library

<400> SEQUENCE: 14
cgtacaagct tcgatcctcc acctcccgag ccacctccgc ctgaaccgcc tccaccgcca     60
atggcactca gcgcatg                                                    77
```

<210> SEQ ID NO 15
<211> LENGTH: 32
<212> TYPE: DNA
<213> ORGANISM: Unknown
<220> FEATURE:
<223> OTHER INFORMATION: DD5-1 mammalian primer used to amplify the
    DOPA decarboxylase (DD) gene from cDNA library

<400> SEQUENCE: 15
acgcaaagct tatgaacgca agtgaattcc ga                                32

<210> SEQ ID NO 16
<211> LENGTH: 34
<212> TYPE: DNA
<213> ORGANISM: Unknown
<220> FEATURE:
<223> OTHER INFORMATION: DD3-1 mammalian primer used to amplify the
    DOPA decarboxylase (DD) gene from cDNA library

<400> SEQUENCE: 16
ctggactagt ctactccctc tctgctcgca gcac                              34

<210> SEQ ID NO 17
<211> LENGTH: 32
<212> TYPE: DNA
<213> ORGANISM: Unknown
<220> FEATURE:
<223> OTHER INFORMATION: DD5-2 mammalian primer used to amplify the
    DOPA decarboxylase (DD) gene from cDNA library

<400> SEQUENCE: 17
cacagtcgac catgaacgca agtgaattcc ga                                32

<210> SEQ ID NO 18
<211> LENGTH: 77
<212> TYPE: DNA
<213> ORGANISM: Unknown
<220> FEATURE:
<223> OTHER INFORMATION: DD3-2 mammalian primer used to amplify the
    DOPA decarboxylase (DD) gene from cDNA library

<400> SEQUENCE: 18
cgtacaagct tcgatcctcc acctcccgag ccacctccgc ctgaaccgcc tccaccctcc  60
ctctctgctc gcagcac                                                 77

<210> SEQ ID NO 19
<211> LENGTH: 33
<212> TYPE: DNA
<213> ORGANISM: Unknown
<220> FEATURE:
<223> OTHER INFORMATION: TH5-2 mammalian primer used to amplify the
    tyrosine hydroxyase (TH) gene from cDNA library

<400> SEQUENCE: 19
acgcaaagct tatgcccacc cccgacgcca cca                               33

<210> SEQ ID NO 20
<211> LENGTH: 34
<212> TYPE: DNA
<213> ORGANISM: Unknown
<220> FEATURE:
<223> OTHER INFORMATION: TH3-2 mammalian primer used to amplify the
    tyrosine hydroxyase (TH) gene from cDNA library

<400> SEQUENCE: 20
ctggactagt ctagccaatg gcactcagcg catg                                      34

```
<210> SEQ ID NO 21
<211> LENGTH: 15
<212> TYPE: PRT
<213> ORGANISM: Artificial Sequence
<220> FEATURE:
<223> OTHER INFORMATION: flexible linker sequence used to link fusion
      proteins

<400> SEQUENCE: 21
```

Gly Gly Gly Gly Ser Gly Gly Gly Gly Ser Gly Gly Gly Gly Ser
1               5                   10                  15

```
<210> SEQ ID NO 22
<211> LENGTH: 25
<212> TYPE: PRT
<213> ORGANISM: Artificial Sequence
<220> FEATURE:
<223> OTHER INFORMATION: flexible linker sequence used to link fusion
      proteins

<400> SEQUENCE: 22
```

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

```
<210> SEQ ID NO 23
<211> LENGTH: 26
<212> TYPE: PRT
<213> ORGANISM: Saccharomyces cerevisiae

<400> SEQUENCE: 23
```

Asn Phe Ile Arg Gly Arg Glu Asp Leu Leu Gly Lys Ile Ile Arg Gln
1               5                   10                  15

Lys Ile Ile Arg Gln Lys Gly Ser Ser Asn
            20                  25

```
<210> SEQ ID NO 24
<211> LENGTH: 23
<212> TYPE: PRT
<213> ORGANISM: Artificial Sequence
<220> FEATURE:
<223> OTHER INFORMATION: flexible linker sequence used to link fusion
      proteins

<400> SEQUENCE: 24
```

Asn Leu Ser Ser Asp Ser Ser Leu Ser Ser Pro Ser Ala Leu Asn Ser
1               5                   10                  15

Pro Gly Ile Glu Gly Leu Ser
            20

```
<210> SEQ ID NO 25
<211> LENGTH: 14
<212> TYPE: PRT
<213> ORGANISM: Artificial Sequence
<220> FEATURE:
<223> OTHER INFORMATION: flexible linker sequence used to link fusion
      proteins

<400> SEQUENCE: 25
```

Gln Gly Ala Thr Phe Ala Leu Arg Gly Asp Asn Pro Gln Gly
1               5                   10

```
-continued

<210> SEQ ID NO 26
<211> LENGTH: 18
<212> TYPE: PRT
<213> ORGANISM: Artificial Sequence
<220> FEATURE:
<223> OTHER INFORMATION: flexible linker sequence used to link fusion
      proteins

<400> SEQUENCE: 26

Ser Gly Gly Gly Glu Ile Leu Asp Val Pro Ser Thr Gly Gly Ser Ser
1               5                   10                  15

Pro Gly

<210> SEQ ID NO 27
<211> LENGTH: 43
<212> TYPE: DNA
<213> ORGANISM: Human immunodeficiency virus

<400> SEQUENCE: 27
gctaattcac tcccaaagaa gacaggcctg ctagcttaag taa                        43

<210> SEQ ID NO 28
<211> LENGTH: 17
<212> TYPE: DNA
<213> ORGANISM: Human immunodeficiency virus

<400> SEQUENCE: 28
tcactcgggg cgccagt                                                    17
```